(12) United States Patent
Leach et al.

(10) Patent No.: US 9,937,634 B2
(45) Date of Patent: *Apr. 10, 2018

(54) COMPOSITIONS AND METHODS FOR TREATING CELLULOSE-BASED MATERIALS WITH MICRONIZED ADDITIVES

(71) Applicant: Koppers Performance Chemicals Inc., Pittsburgh, PA (US)

(72) Inventors: Robert M. Leach, Grand Island, NY (US); Jun Zhang, Peachtree City, GA (US)

(73) Assignee: Koppers Performance Chemicals Inc., Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/995,624

(22) Filed: Jan. 14, 2016

(65) Prior Publication Data

US 2016/0325458 A1 Nov. 10, 2016

Related U.S. Application Data

(60) Continuation of application No. 14/608,800, filed on Jan. 29, 2015, now Pat. No. 9,266,251, which is a
(Continued)

(51) Int. Cl.
*B27K 3/32* (2006.01)
*B27K 3/22* (2006.01)
(Continued)

(52) U.S. Cl.
CPC .............. *B27K 3/005* (2013.01); *A01N 25/12* (2013.01); *B27K 3/08* (2013.01); *B27K 3/15* (2013.01);
(Continued)

(58) Field of Classification Search
None
See application file for complete search history.

(56) References Cited

U.S. PATENT DOCUMENTS

| | | |
|---|---|---|
| 1,388,513 A | 8/1921 | Chandler |
| 1,999,458 A | 4/1935 | Hollister |
| (Continued) | | |

FOREIGN PATENT DOCUMENTS

| | | |
|---|---|---|
| CA | 2103470 A1 | 8/1994 |
| DE | 4112652 A1 | 10/1992 |
| (Continued) | | |

OTHER PUBLICATIONS

Backman, P.A., et al., "The Effects of Particle Size and Distribution on Performance of the Fungicide Chlorothalonil, Phytopathology," St. Paul, MD, US, vol. 66, No. 10, Jan. 1, 1976, pp. 1242-1245, XP009062911.

(Continued)

*Primary Examiner* — Joseph D Anthony
(74) *Attorney, Agent, or Firm* — Covington & Burling LLP

(57) ABSTRACT

A composition for treating cellulosic materials is provided. The composition comprises a dispersion of micronized additives. The dispersion comprises additive particles with diameters in the range of 0.001 to 25 microns. Also provided is a method for the application of the additive-containing composition to wood, as well as wood products which have been treated with the composition.

8 Claims, 2 Drawing Sheets

Coniferous Wood Anatomy

Related U.S. Application Data division of application No. 14/069,651, filed on Nov. 1, 2013, now Pat. No. 8,974,854, which is a continuation of application No. 13/074,170, filed on Mar. 29, 2011, now Pat. No. 8,603,576, which is a division of application No. 12/638,407, filed on Dec. 15, 2009, now abandoned, which is a division of application No. 11/126,839, filed on May 11, 2005, now abandoned.

(60) Provisional application No. 60/570,659, filed on May 13, 2004.

(51) Int. Cl.
| | |
|---|---|
| B27K 3/26 | (2006.01) |
| B27K 3/00 | (2006.01) |
| A01N 25/12 | (2006.01) |
| C09D 5/14 | (2006.01) |
| B27K 3/15 | (2006.01) |
| B27K 3/36 | (2006.01) |
| B27K 3/52 | (2006.01) |
| B27K 5/02 | (2006.01) |
| B27K 3/08 | (2006.01) |
| B27K 3/16 | (2006.01) |
| B27K 3/34 | (2006.01) |

(52) U.S. Cl.
CPC .......... *B27K 3/22* (2013.01); *B27K 3/26* (2013.01); *B27K 3/32* (2013.01); *B27K 3/36* (2013.01); *B27K 3/52* (2013.01); *B27K 5/02* (2013.01); *C09D 5/14* (2013.01); *B27K 3/16* (2013.01); *B27K 3/34* (2013.01); *B27K 2240/20* (2013.01); *B27K 2240/30* (2013.01); *B27K 2240/90* (2013.01); *Y10T 428/25* (2015.01); *Y10T 428/254* (2015.01); *Y10T 428/256* (2015.01); *Y10T 428/268* (2015.01); *Y10T 428/2982* (2015.01); *Y10T 428/31895* (2015.04); *Y10T 428/31989* (2015.04); *Y10T 428/662* (2015.04)

(56) References Cited

U.S. PATENT DOCUMENTS

| | | | |
|---|---|---|---|
| 2,194,827 A | 3/1940 | Gordon | |
| 2,558,304 A | 6/1951 | Marcot et al. | |
| 2,573,253 A | 10/1951 | Farber | |
| 3,007,844 A | 11/1961 | Schulz | |
| 3,231,464 A | 1/1966 | Dettwiler et al. | |
| 3,535,423 A | 10/1970 | Ordas | |
| 3,816,307 A | 6/1974 | Woods | |
| 3,945,835 A | 3/1976 | Clarke et al. | |
| 3,968,276 A | 7/1976 | Allen | |
| 4,058,607 A | 11/1977 | Hennart et al. | |
| 4,062,991 A | 12/1977 | Kyte et al. | |
| 4,142,009 A | 2/1979 | Kyte et al. | |
| 4,310,590 A | 1/1982 | Petigara | |
| 4,313,976 A | 2/1982 | Leach | |
| 4,539,047 A | 9/1985 | Crockatt et al. | |
| 4,622,248 A | 11/1986 | Leach et al. | |
| RE32,329 E | 1/1987 | Paszner | |
| 4,649,065 A | 3/1987 | Hein et al. | |
| 4,663,364 A | 5/1987 | Iwasaki et al. | |
| 4,702,776 A | 10/1987 | Hoffner et al. | |
| 4,741,971 A | 5/1988 | Beck et al. | |
| 4,897,427 A | 1/1990 | Barnavon et al. | |
| 4,923,894 A | 5/1990 | Kanda et al. | |
| 4,935,457 A | 6/1990 | Metzner et al. | |
| 5,098,472 A | 3/1992 | Watkins et al. | |
| 5,196,407 A | 3/1993 | Goletz et al. | |
| 5,207,823 A | 5/1993 | Shiozawa | |
| 5,277,979 A | 1/1994 | Kielbania, Jr. et al. | |
| 5,304,376 A | 4/1994 | Friedrichs et al. | |
| 5,342,438 A | 8/1994 | West | |
| 5,424,077 A | 6/1995 | Lajoie | |
| 5,438,034 A | 8/1995 | Walker | |
| 5,462,589 A | 10/1995 | Nicholas et al. | |
| 5,484,934 A | 1/1996 | Ikeda et al. | |
| 5,527,384 A | 6/1996 | Williams et al. | |
| 5,536,305 A | 7/1996 | Yu | |
| 5,552,378 A | 9/1996 | Trinh et al. | |
| 5,635,217 A | 6/1997 | Goettsche et al. | |
| 5,667,795 A | 9/1997 | Fraley et al. | |
| 5,714,507 A | 2/1998 | Valcke et al. | |
| 5,763,364 A | 6/1998 | Frisch et al. | |
| 5,833,741 A | 11/1998 | Walker | |
| 5,874,025 A | 2/1999 | Heuer et al. | |
| 5,874,476 A | 2/1999 | Hsu et al. | |
| 5,879,025 A | 3/1999 | Blumenthal | |
| 5,972,266 A | 10/1999 | Fookes et al. | |
| 5,990,043 A | 11/1999 | Kugler et al. | |
| 6,110,263 A | 8/2000 | Goettsche et al. | |
| 6,123,756 A | 9/2000 | Poppen et al. | |
| 6,274,199 B1 | 8/2001 | Preston et al. | |
| 6,306,202 B1 | 10/2001 | West | |
| 6,352,583 B1 | 3/2002 | Goettsche et al. | |
| 6,482,814 B1 | 11/2002 | Bath et al. | |
| 6,485,790 B2 | 11/2002 | Walker et al. | |
| 6,503,306 B1 | 1/2003 | Watkins | |
| 6,514,512 B1 | 2/2003 | Puterka et al. | |
| 6,521,288 B2 * | 2/2003 | Laks ................... | A01N 25/12 427/180 |
| 6,541,038 B1 | 4/2003 | Tanaka et al. | |
| 6,558,685 B1 | 5/2003 | Kober et al. | |
| 6,576,661 B1 | 6/2003 | Bruck et al. | |
| 6,585,989 B2 | 7/2003 | Herbst et al. | |
| 6,753,035 B2 | 6/2004 | Laks et al. | |
| 6,849,276 B1 | 2/2005 | Dufau et al. | |
| 6,896,908 B2 | 5/2005 | Lloyd et al. | |
| 6,905,531 B2 | 6/2005 | Richardson et al. | |
| 6,905,532 B2 | 6/2005 | Richardson et al. | |
| 7,316,738 B2 | 1/2008 | Richardson et al. | |
| 7,408,003 B2 | 8/2008 | Brown et al. | |
| 7,449,130 B2 | 11/2008 | Lloyd et al. | |
| 7,632,567 B1 * | 12/2009 | Zhang ................... | A01N 59/16 106/18.32 |
| 7,674,481 B2 * | 3/2010 | Leach ................... | A01N 25/04 424/630 |
| 8,603,576 B2 * | 12/2013 | Leach ................... | A01N 25/12 106/15.05 |
| 8,974,854 B2 * | 3/2015 | Leach ................... | A01N 25/12 106/15.05 |
| 9,266,251 B2 * | 2/2016 | Leach ................... | A01N 25/12 |
| 2002/0021892 A1 | 2/2002 | Ambrosi et al. | |
| 2002/0051892 A1 | 5/2002 | Laks et al. | |
| 2002/0128367 A1 * | 9/2002 | Daisey, Jr. ............. | B05D 7/08 524/487 |
| 2004/0258767 A1 | 12/2004 | Leach et al. | |
| 2004/0258768 A1 * | 12/2004 | Richardson ........... | A01N 59/20 424/630 |
| 2004/0258838 A1 | 12/2004 | Richardson et al. | |
| 2005/0013939 A1 | 1/2005 | Vinden et al. | |
| 2005/0107467 A1 | 5/2005 | Richardson | |
| 2005/0118280 A1 | 6/2005 | Leach et al. | |
| 2005/0130866 A1 | 6/2005 | Richardson et al. | |
| 2005/0152994 A1 | 7/2005 | Leach et al. | |
| 2005/0182152 A1 | 8/2005 | Nonninger et al. | |
| 2005/0249812 A1 | 11/2005 | Leach et al. | |
| 2005/0252408 A1 | 11/2005 | Richardson et al. | |
| 2005/0255251 A1 | 11/2005 | Hodge et al. | |
| 2005/0256026 A1 | 11/2005 | Hodge et al. | |
| 2005/0265893 A1 | 12/2005 | Leach et al. | |
| 2006/0062926 A1 | 3/2006 | Richardson et al. | |
| 2006/0075921 A1 | 4/2006 | Richardson et al. | |
| 2006/0075923 A1 | 4/2006 | Richardson | |
| 2006/0078686 A1 | 4/2006 | Hodge et al. | |
| 2006/0086284 A1 | 4/2006 | Zhang et al. | |
| 2006/0086841 A1 | 4/2006 | Richardson et al. | |
| 2006/0112850 A1 | 6/2006 | Zhang et al. | |
| 2006/0147632 A1 | 7/2006 | Zhang et al. | |

(56) References Cited

U.S. PATENT DOCUMENTS

| | | |
|---|---|---|
| 2006/0217447 A1 | 9/2006 | Blow |
| 2006/0257578 A1 | 11/2006 | Zhang et al. |
| 2006/0276468 A1 | 12/2006 | Blow |

FOREIGN PATENT DOCUMENTS

| | | |
|---|---|---|
| EP | 0472973 A1 | 3/1992 |
| EP | 1034903 A1 | 9/2000 |
| GB | 1491330 A | 11/1977 |
| JP | 61-246002 A | 11/1986 |
| JP | S62-39201 | 2/1987 |
| JP | S62-116102 | 5/1987 |
| JP | S64-026401 A | 1/1989 |
| JP | 10-272610 A | 10/1998 |
| JP | 2000-102907 A | 4/2000 |
| SE | 379167 B | 9/1975 |
| WO | WO-85/00040 A1 | 1/1985 |
| WO | WO-00/05955 A1 | 2/2000 |
| WO | WO-00/24259 A1 | 5/2000 |
| WO | WO-00/24528 A1 | 5/2000 |
| WO | WO-00/78281 A1 | 12/2000 |
| WO | WO-01/91925 A1 | 12/2001 |
| WO | WO-02/06417 A1 | 1/2002 |
| WO | WO-03/102090 A2 | 12/2003 |
| WO | WO-03/103392 A1 | 12/2003 |

OTHER PUBLICATIONS

Supplementary European Search Report for PCT/US2005/016503 dated Feb. 2, 2009.
Supplementary European Search Report for PCT/US2005/037303 dated Feb. 5, 2009.
Koch, C.C., Synthesis of Nanostructured Materials by Mechanical Milling: Problems and Opportunities, NanoStructured Materials, vol. 9, pp. 13-22, 1997.
American Wood-Preservers' Association Standard E7-07, "Standard Method of Evaluating Preservatives by Filed Tests with Stakes," 2006.
American Wood-Preservers' Association Standard E10-01, "Standard Method of Testing Wood Preservatives by Laboratory Soil-Block Cultures," 2005.
The Merck Index (12th Ed. 1996) Merck & Co., Inc.
Davis, Food Storage and Preservative-Treated Wood, Alaska Science Forum (Mar. 10, 1980) [online][retrieved on Nov. 10, 2008].. URL:http://www.gi.alaska.edu/Science Forum/ASF3/380.htm/.
STN online, file SCISEARCH, Acc. No. 1993:540390 (Siegfried, Comparative Toxicity of Pyrethoid Insecticides to Terrestial and Aquatic Insects, Environmental Toxicology and Chemistry (1993), vol. 12, No. 9, pp. 1683-1689.
Superior Court of New Jersey, Decision After Trial, *Phibro-Tech, Inc.* v. *Osmose Holdings, Inc.*, docket No. C-365-05, Jun. 25, 2007.
Superior Court of New Jersey, Chancery Division, Final Judgment, *Phibro-Tech, Inc.* v. *Osmose Holdings, Inc., Osmose, Inc.* , docket No. C-365-05, Aug. 14, 2007.
Liu, Y., et al., Use of Nanoparticles for the Controlled Release of Biocides in Pressure-Treated Solid Wood, Polymer Preprints 38(2), 1997, pp. 624-625.
Liu, Y., et al., Michigan Technical Univ., Dept. of Chemistry, Houghton, MI, Use of Polymeric Nanoparticles for Controlled Release of Biocides in Solid Wood, Materials Research Society Symposium Proceedings Series; 1998, vol. 550, Abstract GG3.4.
Liu, Y., et al., "Use of Polymer Nanoparticles as Carriers for the Controlled release of Biocides in Solid Wood". Ph.D. Dissertation of Yong Liu; Michigan Technological University, Houghton, MI, 1999.
Liu, Y., et al., Use of Nanoparticles for Controlled Release of Biocides in Solid Wood, Journal of Applied Polymer Science, vol. 79, 2001, pp. 458-465.
Lide, Characteristics of Particles and Particles Dispersoids Handbook of Chemistry and Physics, 75th edition; 1994, Florida: CRC Press, pp. 15-38.
Shaw, www.fda.gov/ohmrms/dockets/ac/01/slides/3763s2_09_shaw.ppt; 2001.
Hawley's Condensed Chemical Disctionary, 14th Edition, John Wiley & Son, Inc., 2001, p. 86.
JP Published Unexamined Patent Application No. S61-246002 (Nov. 1, 1986).
JP Published Unexamined Patent Application No. S61-244502 (Oct. 30, 1986).
Patent Assignment Abstract of Title for U.S. Appl. No. 11/299,522 Recorded Mar. 16, 2006.
Patent Assignment Abstract of Title for U.S. Appl. No. 10/281,326 Recorded Aug. 16, 2004.
Wikipedia entry for "tributyltin oxide" (2011).
The Australian Clay Minerals Society, "About Clays," (http://www.clays.org.au/mins.htm) printed website on Nov. 18, 2011.
Dev et al., "Termite resistance and permanency tests on zinc-borate—an environmental friendly preservative," J. Tim. Dev. Assoc. (India), 43(2): 10-15 (Apr. 1997).
Colortrend® 888/817 brochure by Degussa (Mar. 2003).
Material Safety Data Sheet: Colortrend 888-1045 F-Red Oxide (effective Jan. 17, 1995).

\* cited by examiner

Coniferous Wood Anatomy

Bordered Pit

COMPOSITIONS AND METHODS FOR TREATING CELLULOSE-BASED MATERIALS WITH MICRONIZED ADDITIVES

CROSS REFERENCE TO RELATED APPLICATION

This application is a continuation of U.S. application Ser. No. 14/608,800, filed on Jan. 29, 2015, which is a divisional of U.S. application Ser. No. 14/069,651, filed on Nov. 1, 2013, now U.S. Pat. No. 8,974,854, which is a continuation of U.S. application Ser. No. 13/074,170, filed Mar. 29, 2011, now U.S. Pat. No. 8,603,576, which is a divisional of U.S. application Ser. No. 12/638,407, filed Dec. 15, 2009, now abandoned, which is a divisional of U.S. application Ser. No. 11/126,839, filed May 11, 2005, now abandoned, which claims the benefit under 35 U.S.C. § 119(e) of U.S. Provisional Application No. 60/570,659, filed May 13, 2004, all of which are herein incorporated by reference in their entireties.

BACKGROUND

Wood and wood-based substrates, such as paper, particleboard, wood composites, plastic lumbers, rope, etc., are often treated in order to impart desired characteristics to or enhance existing characteristics of the substrate. Non-limiting examples of performance characteristics which can be imparted or enhanced by treatment of a substrate with additives are durability, fire resistance and water resistance. Non-limiting examples of such appearance characteristics are color and texture. Non-limiting examples of additives which can be applied are colorants, pigments, polymers, water repellants, dimensional stabilizing agents, UV inhibitors, UV absorbers, UV blockers, antioxidants, fire retardants and biocides, such as, for example, insecticides, fungicides, moldicides, algaecides and bactericides.

Many, if not most such additives have little or no water solubility and are thus difficult to apply to wood as a water-based solution. Generally, such additives have been dissolved in organic carriers prior to use, often with the additional step of emulsification in water by the use of various surfactants if a water-based application is desired.

Solubilizing agents or surfactants such as emulsifying agents, wetting agents, etc. are added in order to give a product that can be applied as a water-based composition to wood or cellulosic substrates. However, solubilizing agents or surfactants, etc. are costly and the use of these products may also result in enhanced leaching of additive upon exposure of treated wood to moisture. It is thought that the enhanced leaching is due to the fact that solubilizing agents, surfactants, emulsifying agents, wetting agents, etc. remain in the wood after treatment. Upon exposure to moisture, the additives are solubilized or otherwise mobilized, and leach from the wood.

Despite the efforts of many inventors, there remains a need for organic preservative systems which do not require organic solubilizing agents, which are suitable for use in the treatment wood and cellulose-based materials, and have only low levels of leaching, if any, upon exposure of treated materials to the environment. This need is satisfied by the compositions disclosed herein.

SUMMARY OF THE INVENTION

Disclosed herein are compositions which comprise micronized additives. Also disclosed is a method for the use of the compositions to treat cellulosic materials, particularly wood.

Current technology typically requires the addition of organic solvents, emulsifying agents, etc. Disadvantages of the typical approach used in the art include increased cost, residue bleeding, environmental damage and harmful exposure to leached additive.

With the inventive compositions disclosed herein, organic solvents and emulsifiers are not required, thus reducing cost. Furthermore, leaching of additives from treated materials is reduced relative to non-micronized or solubilized compositions currently used in the art, thus reducing environmental and exposure risks.

Also provided is a method for the treatment of wood or wood product with the compositions of the present invention. In one embodiment, the method comprises the steps of 1) providing a mixture comprising micronized additive particles in an aqueous carrier, such as in the form of a dispersion, emulsion, suspension, or other particle/carrier combination, and 2) applying the particles to a wood or wood product. In a further embodiment, the particulate additives have been prepared by the grinding of the additive, optionally in non-micronized particulate form, in wetting agents and/or dispersants such that the additive is reduced to the form of micronized particles. When such a composition is used for preservation of wood, there is minimal leaching of the additive from wood as described herein.

Figure 1:
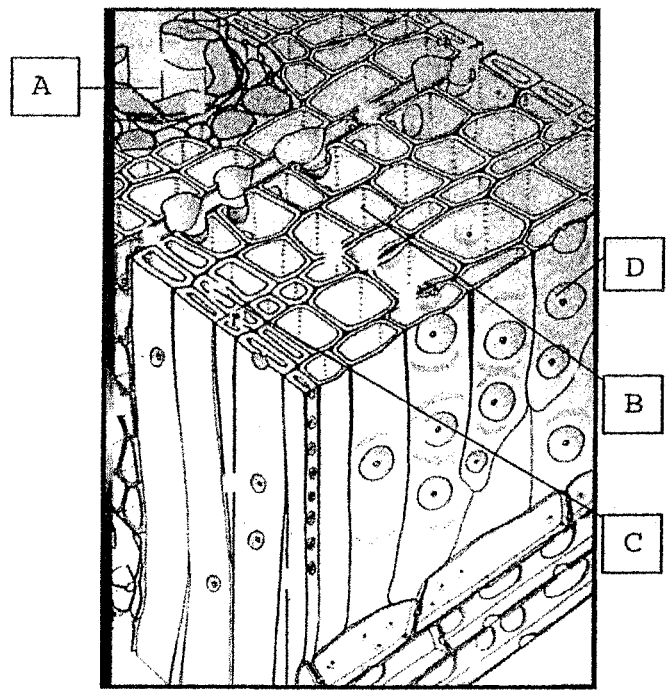
FIG. 1 depicts the anatomy of coniferous wood. A: Resin canal; B: Earlywood tracheids; C: Latewood tracheids; D: Bordered pits.

RIGHT: Microscopic view of the cross section of a bordered pit.

LEFT: Torus in top view. The torus is supported by a net of radial fibril membrane, also called the margo. The flow of fluids between two tracheids through such a membrane is restricted by the size of the membrane openings. A: Pit aperture; B: Torus; C: Margo (microfibrils); D: Pit border.

DETAILED DESCRIPTION OF THE INVENTION

Unless stated otherwise, such as in the examples, all amounts and numbers used in this specification are intended to be interpreted as modified by the term "about." Likewise, elements or compounds identified in this specification, unless stated otherwise, are intended to be non-limiting and representative of other elements or compounds generally considered by those skilled in the art as being within the same family of elements or compounds. Also, the term "additive" refers to water repellants, coloring agents, UV stabilizers, UV absorbers, UV blockers, antioxidants, dimensional stabilizing agents, fire retardants or other organic or inorganic compounds which enhance appearance or performance characteristics of the wood.

Disclosed herein is a micronized additive composition and method for use thereof in treatment of cellulosic material, and in a preferred embodiment, wood. Unlike wood which has been treated with additives solubilized in organic solvents or other solubilizing agents, wood treated with compositions of the present invention have little or no emission of organic solvent. Furthermore, upon exposure to moisture, the leaching of the additive from treated wood is generally significantly less than that associated with solubilized compositions.

Non-limiting examples of additives which can be used are inorganic or organic additives, such as organic pigments, inorganic pigments, waxes, polymers, anti-weathering agents (such as, for example, UV absorbers, UV blockers, UV inhibitors, antioxidants), fire retardants and mixtures thereof. Non-limiting examples of additive chemical types to which this strategy has been applied are azoles, carbamates, isothiazolinones, thiocyanates, sulfenamides, quaternary phosphonium compounds, quaternary ammonium compounds, nitriles, pyridines, etc. and mixtures thereof.

Inorganic or organic pigments, water repellants, anti-weathering agents, dimensional stabilization agents, and fire retardants, etc. and mixtures or synergistic mixtures thereof having relatively low solubility can be used with the system and are well known to those skilled in the art and include those listed in the tables below. In general, it is preferable for the additive to comprise particles of sizes in the range of 0.001 microns to 25 microns and a relatively low solubility in water. A water solubility which is less than 0.5 g of biocide per 100 grams of water at 25° C. is preferred. Such additives are referred to hereafter as "suitably insoluble."

In general, an "additive" is defined to be a component which is applied to wood as part of a solution. In an embodiment of the present invention, the additive is in addition to a component which has biocidal activity. An additive can, itself, have biocidal ability, and be a co-biocide. An additive may instead be a non-biocidal compound included to enhance the performance or appearance characteristics of the wood to which it is to be applied. An additive may also be a component which does both, i.e., has biocidal activity and also improves an appearance characteristic of the wood. Those of skill in the art will recognize that many compounds have both characteristics.

Non-limiting examples of suitably insoluble inorganic pigments include: iron oxides, including red iron oxides, yellow iron oxides, black iron oxides and brown iron oxides; carbon black, iron hydroxide, graphite, black micaceous iron oxide; aluminum flake pigments, pearlescent pigments; calcium carbonate; calcium phosphate; calcium oxide; calcium hydroxide; bismuth oxide; bismuth hydroxide; bismuth carbonate; copper carbonate; copper hydroxide; basic copper carbonate; silicon oxide; zinc carbonate; barium carbonate; barium hydroxide; strontium carbonate; zinc oxide; zinc phosphate; zinc chromate; barium chromate; chrome oxide; titanium dioxide; zinc sulfide and antimony oxide.

Non-limiting examples of organic pigments include Monoazo (arylide) pigments such as PY3, PY65, PY73, PY74, PY97 and PY98; Disazo (diarylide); Disazo condensation; Benzimidazolone; Beta Naphthol; Naphthol; metal-organic complexes; Isoindoline and Isoindolinone; Quinacridone; perylene; perinone; anthraquinone; diketo-pyrrolo pyrrole; dioxazine; triacrylcarbonium; the phthalocyanine pigments, such as cobalt phthalocyanine, copper phthalocyanine, copper semichloro- or monochlorophthalocyanine, copper phthalocyanine, metal-free phthalocyanine, copper polychlorophthalocyanine, etc.; organic azo compounds; organic nitro compounds; polycyclic compounds, such as phthalocyanine pigments, quinacridone pigments, perylene and perinone pigments; diketopyrrolo-pyrrole (DPP) pigments; thioindigo pigments; dioxazine pigments; quinophthalone pigments; triacrylcarbonium pigments, and Diaryl pyrrolopyroles, such as PR254.

Non-limiting examples of suitably insoluble organic pigments, grouped according to the color they produce (e.g. blues, blacks, greens, yellow, reds and browns), based on their color index include: Pigment Yellows 11, 3, 12, 13, 14, 17, 81, 83, 65, 73, 74, 75, 97, 111, 120, 151, 154, 175, 181, 194, 93, 94, 95, 128, 166, 129, 153, 109, 110, 173, 139, 185, 138, 108, 24; Pigment Oranges 5, 36, 60, 62, 65, 68, 61, 38, 69, 31, 13, 34, 43, 51, 71, 73; Pigment Reds 3, 4, 171, 175, 176, 185, 208, 2, 5, 12, 23, 112, 146, 170, 48, 57, 60, 68, 144, 166, 214, 220, 221, 242, 122, 192, 202, 207, 209, 123, 149, 178, 179, 190, 224, 177, 168, 216, 226, 254, 255, 264, 270, 272; Pigment Violets 32, 19, 29, 23, 37; Pigment Browns 25, 23; Pigment Blacks 1, 31, 32, 20; Pigment Blues 15, 15:1, 15:2, 15:3, 15:4, 15:6, 16, 60; and Pigment Greens 7, 36.

Non-limiting examples of suitably insoluble water repellents include paraffin wax, olefin wax, petroleum wax, carnauba wax; polyethylene wax, silicone wax, polypropylene wax, PTFE wax and synthetic wax.

Non-limiting examples of suitably insoluble anti-weathering agents include pigments such as zinc oxide, zinc sulfide, iron oxide, carbon black, titanium dioxide; UV absorbers such as hydroxyl-substituted benzophenones, hydroxyphenyl benzotriazides, substituted acrylonitriles; UV stabilizers such as hindered amine light stabilizers (HALS); and anti-oxidants such as amines, imidiazoles or complex hindered phenolics.

Non-limiting examples of suitably insoluble dimensional stabilization agents include waxes such as paraffin wax, olefin wax, petroleum wax, carnauba wax, polyethylene wax, silicone wax, polypropylene wax, PTFE wax and synthetic wax, and polymers such as polystyrene, polyethylene, polypropylene, polyvinyl chloride, polyacrylonitrile, polyvinyl acetate, polyester, acrylic polymers, polyamide, polyurethane, phenolic novolacs, phenolic resoles, urea formaldehyde resins, melamine formaldehyde resins, epoxy resins, natural resins such as rosin and rosin esters, hydrocarbon resins, ketone resins, terpene resins, alkyd resins, silicone resins and silicate resins, and other water insoluble polymers.

Non-limiting examples of suitably insoluble fire retardants are: metal hydroxides such as aluminum trihydroxide and magnesium hydroxide; antimony compounds such as antimony trioxide, antimony pentoxide and calcium antimonite; zinc compounds such as zinc stannate, zinc hydroxylstannate, zinc borate, zinc silicate, zinc phosphate, zinc oxide and zinc hydroxide; phosphorous based compounds such as phosphate esters red phosphorus melamine phosphate, zinc phosphate, calcium phosphate, magnesium phosphate and ethylenediamine phosphate; silicate compounds such as calcium silicate, silica, magnesium silicate and zinc silicate; halogenated compounds such as tetra bromo bisphenol A; nitrogen based compounds such as melamine and its salts, melamine borate and polyamides.

Inorganic metal compounds, many having a degree of biocidal activity, can be used as additives in the compositions of the present invention. Non-limiting examples of such additives are suitably insoluble compounds of, for example, copper, tin, silver, nickel. For example, non-limiting examples of specific suitably insoluble metal compounds include cuprous oxide, cupric oxide, copper hydroxide, copper carbonate, basic copper carbonate, copper oxychloride, copper 8-hydroxyquinolate, copper dimethyldithiocarbamate, copper omadine, and copper borate.

The micronized additive can be obtained by grinding the additive, optionally wetted or present as a dispersion, to the desired particle size using a grinding mill. Other particulating methods known in the art can also be used, such as high speed, high shear mixing or agitation. The resulting particulate additive can be mixed with water or other aqueous liquid carrier to form a solution of dispersed additive particles. Optionally, the: solution can comprise a thickener, such as, for example, a cellulose derivative, as is known in the art. The solution can, optionally, additionally comprise other biocides, organic or inorganic, micronized if desired, to produce a formulation suitable for the preservation of wood and other cellulose-based materials.

The particles are preferably dispersed in a dispersant, such as acrylic copolymers, aqueous solution of copolymers with pigment affinity groups, modified polyacrylate, acrylic polymer emulsions, modified lignin and the like. If desired, a stabilizer as is known in the art can be used.

The penetration of the dispersion formulation into the cellular structure of wood or other cellulose-based material is dependent upon particle size considerations. If the inorganic/organic additive source used in formulating the dispersion formulation disclosed herein has a particle size in excess of 30 microns, the particles may be filtered by the surface of the wood and thus may not be uniformly distributed within the cell and cell wall. As shown in FIG. 1, the primary entry and movement of fluids through wood tissue occurs primarily through the tracheids and border pits. Tracheids have a diameter of about thirty microns. Fluids are transferred between wood cells by means of border pits.

Without desiring to be bound by theory, penetration of the micronized dispersion formulation into wood takes place because particles migrate into or are taken up by tracheids in the wood. FIG. 1 shows the physiological structure of wood. As shown in FIG. 1, the primary entry and movement of fluids through wood tissue occurs primarily through the tracheids and border pits. Fluids are transferred between wood cells by means of border pits. Wood tracheids generally have diameters of around 30 microns, and thus good penetration can be achieved by the use of particles having long axis dimensions ("particle size" which are less than the tracheid diameters of the wood or wood product to be treated). Particles having diameters which are larger than the average diameter of the tracheids will generally not penetrate the wood (i.e., they will be "filtered" by the wood) and may block, or "clog" tracheids from taking in additional particles.

The diameter of the tracheids depends upon many factors, including the identity of the wood. As a general rule, if the additives disclosed herein have a particle size in excess of 25 microns, the particles may be filtered by the surface of the wood and thus may not be uniformly distributed within the cell and cell wall.

Figure 2:
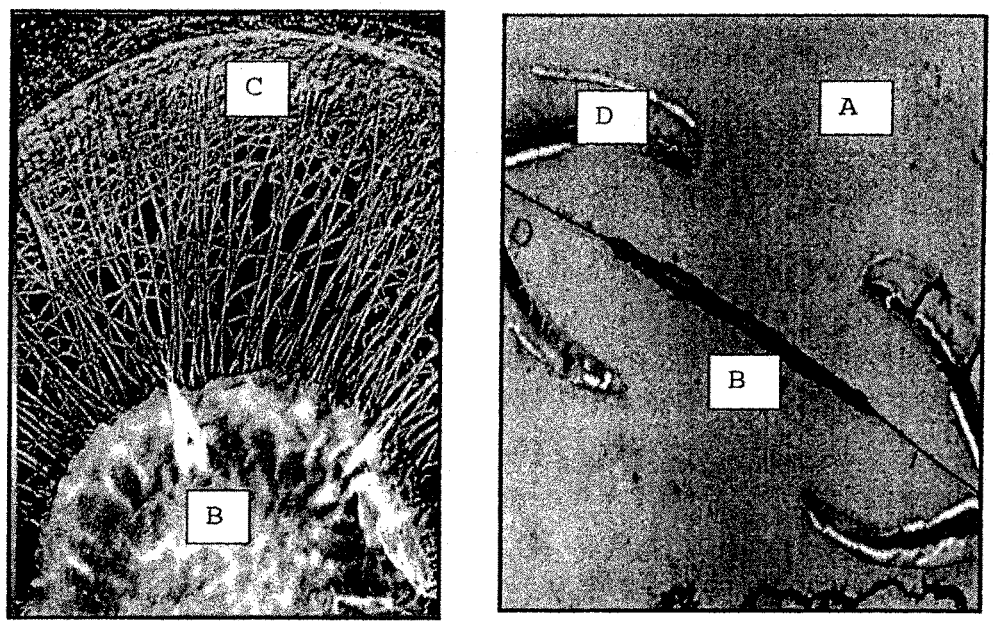
FIG. 2 depicts the border pit structure for coniferous woods.

Studies by Mercury-Porosimetry technique indicated that the overall diameter of the border pit chambers typically varies from a several microns up to thirty microns while, the diameter of the pit openings (via the microfibrils) typically varies from several hundredths of a micron to several microns. FIG. 2 depicts the border pit structure for coniferous woods. Thus, in order to increase penetration and improve the uniformity of distribution of the particulate additive, the particle size should be such that it can travel through the pit openings.

In one embodiment particle size of the micronized particles used in the dispersion formulation disclosed herein can be micronized, i.e., with a long axis dimension between 0.001-25 microns. In another embodiment, the particle size is between 0.001-10 microns. In another embodiment, the particle size is between 0.01 to 10 microns. If superior uniformity of penetration is desired, particle size of the additive used in the dispersion formulation disclosed herein should be between 0.01-1 microns.

In addition to a recommended upper limit of 25 microns, particles which are too small can leach out of the wood over time. It is thus generally recommended that the particulate additive comprise particles which have diameters which are not less than 0.001 microns.

Particles which are too large can clog the wood, preventing it from taking in other particles and particles which are too small can leach from the wood. Thus particle size distributional parameters can affect the uniformity of particle distribution in the wood, as well as the leaching properties of treated wood. It is thus preferable to use particle size distributions which contain relatively few particle sizes outside the range of 0.001 to 25 microns. It is preferred that no more than 20 weight percent of the particles have diameters which are greater than 25 microns. Because smaller particles have an increased chance of leaching from the wood, it is also preferred that no more than 20 wt % of the particles have diameters under 0.001 microns. Regardless of the foregoing recommendations, it is generally preferred that greater than 80 wt % of the particles have a diameter in the range of 0.001 to 25 microns. In more preferred embodiments, greater than 85, 90, 95 or 99 wt percent particles are in the range of 0.001 to 25 microns.

For increased degree of penetration and uniformity of distribution, at least 50 wt % of the particles should have diameters which are less than 10 microns. More preferred are particle distributions which have at least 65 wt % of the particles with sizes of less than 10 microns. In an additional embodiment, less than 20 wt % of the particles have diameters of less than 1 micron.

The present invention also provides a method for preservation of wood. In one embodiment, the method comprises the steps of treating wood with a composition (treating fluid) comprising a dispersion of additive particles. In another embodiment, wood is treated with a composition comprising a dispersion comprised of particles of multiple additives, at least two of said additives having different average particle sizes. The size of the micronized particles of the additives is between 0.001 to 25 microns, preferably between 0.001 to 10 microns, more preferably between 0.01 to 10 microns and most preferably between 0.01 to 1 microns. In another embodiment, the wood is treated with a composition comprising soluble compounds and micronized additives.

The treating fluid may be applied to wood by dipping, soaking, spraying, brushing, or any other means well known in the art. In a preferred embodiment, vacuum and/or pressure techniques are used to impregnate the wood in accord with this invention including the standard processes, such as the "Empty Cell" process, the "Modified Full Cell" process and the "Full Cell" process, and any other vacuum and/or pressure processes which are well known to those skilled in the art.

The standard processes are defined as described in AWPA Standard C1-03 "All Timber Products—Preservative Treatment by Pressure Processes". In the "Empty Cell" process, prior to the introduction of preservative, materials are subjected to atmospheric air pressure (Lowry) or to higher air pressures (Rueping) of the necessary intensity and duration. In the "Modified Full Cell", prior to introduction of preservative, materials are subjected to a vacuum of less than 77 kPa (22 inch Hg) (sea level equivalent). A final vacuum of not less than 77 kPa (22 inch Hg) (sea level equivalent) should be used. In the "Full Cell Process", prior to introduction of preservative or during any period of condition prior to treatment, materials are subjected to a vacuum of not less than 77 kPa (22 inch Hg). A final vacuum of not less than 77 kPa (22 inch Hg) is used.

The following examples are provided to further describe certain embodiment of the disclosure but are in no way limiting to the scope of disclosure.

Example 1

Six hundred grams of red iron oxide, 400 g yellow iron oxide and 10 g carbon black are added to a container containing 2850.0 g of water and 150 g of a commercially available dispersant. The mixture is mechanically stirred for about 20 minutes and then added to a grinding mill. The sample is ground for about 1 hour and a stable dispersion is obtained. The particle size of the dispersed product can be analyzed by Horiba LA-910 Particle Size Distribution Analyzer (PSDA). The average particle size is preferably 0.3 microns with a distribution range of 0.04 µm to 1.5 µm.

The resulting brown iron oxide dispersion can be diluted with water to make a treating fluid containing 1.0% iron oxide. The treating fluid can be used to treat southern pine samples using a full cell process. The treated samples can be oven dried and tested to check uniform distribution of iron oxide throughout the cross sections and for the presence of a uniform brown color.

Example 2

Nine hundred grams of red iron oxide and 100 g yellow iron oxide are added to a container containing 1550 g of water and 150 g of a commercially available dispersant. The mixture is mechanically stirred for about 20 minutes and then added to a grinding mill. The sample is ground for about 1 hour and a stable dispersion is obtained. The particle size of the dispersed product can be analyzed by Horiba LA-910 Particle Size Distribution Analyzer (PSDA). The average particle size is preferably 0.3 microns with a distribution range of 0.005 µm to 1.5 µm.

The resulting dispersion can be diluted with water to make a treating fluid containing 0.5% total iron oxides. The treating fluid can be used to treat southern pine samples using a full cell process. The treated samples can be oven dried and tested to check uniform distribution of iron oxide throughout the cross sections and for the presence of a uniform color.

Example 3

Seven hundred grams of red iron oxide, 200 g yellow iron oxide and 5 g black iron oxide are added to a container containing 2050 g of water and 180 g of a commercially available dispersant. The mixture is mechanically stirred for about 20 minutes and then added to a grinding mill. The sample is ground for about 1 hour and a stable dispersion is obtained. The particle size of the dispersed product can be analyzed by Horiba LA-910 Particle Size Distribution Analyzer (PSDA). The average particle size is preferably 0.35 microns with a distribution range of 0.005 µm to 2.0 µm.

The resulting dispersion can be diluted with water to make a treating fluid containing 0.5% total iron oxides. The treating fluid can be used to treat southern pine samples using a full cell process. The treated samples can be oven dried and tested to check uniform distribution of iron oxide throughout the cross sections and for the presence of a uniform color.

Example 4

Eight hundred grams of yellow iron oxide, 100 g red iron oxide and 15 g organic pigment blue PB 15 are added to a container containing 3000 g of water and 200 g of a commercially available dispersant. The mixture is mechanically stirred for about 20 minutes and then added to a grinding mill. The sample is ground for about 1 hour and a stable dispersion is obtained. The particle size of the dispersed product can be analyzed by Horiba LA-910 Particle Size Distribution Analyzer (PSDA). The average particle size is preferably 0.30 microns with a distribution range of 0.005 µm to 2.0 µm.

The resulting dispersion can be diluted with water to make a treating fluid containing 0.5% total iron oxides. The treating fluid can be used to treat southern pine samples using a full cell process. The treated samples can be oven dried and tested to check uniform distribution of iron oxide throughout the cross sections and for the presence of a uniform color.

Example 5

Five hundred grams of organic pigment yellow PY65, 600 g of organic pigments red PR23 and 15 g organic pigment blue PB 15 are added to a container containing 3000 g of water and 450 g of a commercially available dispersant. The mixture is mechanically stirred for about 20 minutes and then added to a grinding mill. The sample is ground for about 1 hour and a stable dispersion is obtained. The particle size of the dispersed product can be analyzed by Horiba LA-910 Particle Size Distribution Analyzer (PSDA). The average particle size is preferably 0.20 microns with a distribution range of 0.001 µm to 2.0 µm.

The resulting dispersion can be diluted with water to make a treating fluid containing 0.25% total iron oxides. The treating fluid can be used to treat southern pine samples using a full cell process. The treated samples can be oven dried and tested to check uniform distribution of iron oxide throughout the cross sections and for the presence of a uniform color.

Example 6

Eight hundred grams of organic pigment yellow PY 13 and 100 g of organic pigments red PR254 are added to a container containing 4000 g of water and 500 g of a commercially available dispersant. The mixture is mechanically stirred for about 20 minutes and then added to a grinding mill. The sample is ground for about 1 hour and a stable dispersion is obtained. The particle size of the dispersed product can be analyzed by Horiba LA-910 Particle Size Distribution Analyzer (PSDA). The average particle size is preferably 0.23 microns with a distribution range of 0.001 µm to 2.0 µm.

The resulting dispersion can be diluted with water to make a treating fluid containing 0.25% total iron oxides. The treating fluid can be used to treat southern pine samples using a full cell process. The treated samples can be oven dried and tested to check uniform distribution of iron oxide throughout the cross sections and for the presence of a uniform color.

Example 7

Five hundred grams of titanium dioxide is mixed with 450 grams of water and 50 grams of commercially available wetting agents/dispersants. The mixture is mechanically stirred for 5 minutes. The mixture is then placed in a grinding mill and ground for about 30 minutes. A stable dispersion is preferably obtained with an average particle size of 0.29 microns.

Forty grams of the above obtained titanium dioxide dispersion is mixed with 960 g of water and the resulting composition can be used to treat southern pine stakes. The stakes can be tested for effectiveness against UV degradation and discoloration and compared to untreated samples.

Example 8

Three hundred grams of paraffin wax is mixed with 1855 grams of water and 150 grams of dispersants. The mixture is mechanically mixed for about 5 minutes and placed in a grinding mill. The mixture is ground for about 90 minutes and a stable dispersion obtained with an average particle size of 0.282 microns. After grinding, 2000 g of water is added to the dispersion and the final formulation is used to treat wood. The treated samples can be subjected to water repellency test following the procedure described in American Wood Preservers' Association Standard E-4 "Standard Method of Testing Water Repellency of Pressure Treated Wood".

Example 9

One thousand grams of a commercially available acrylic polymer is mixed with 3780 grams of water and 400 grams of wetting agents/dispersants. The mixture is mechanically stirred for about 20 minutes. The mixture is then placed in a grinding mill and ground for about 120 minutes. A stable dispersion is preferably obtained with an average particle size of 0.20 microns.

A treating fluid can be prepared by mixing the above acrylic polymer dispersion with water and used to treat southern pine stakes. The treated stakes can be tested for water repellency.

Example 10

One thousand grams of zinc borate is mixed with 3000 g of water and 200 grams of commercially available wetting agents/dispersants. The mixture is mechanically stirred for 20 minutes. The mixture is then placed in a grinding mill and ground for about 40 minutes. A stable dispersion is preferably obtained with an average particle size of 0.399 microns.

A 3.0% zinc borate treating fluid can be prepared by diluting the above prepared zinc borate dispersion with water. Wood samples can be treated with the 3.0% zinc borate fluid and the treated samples can be oven dried. The samples can be tested for uniform distribution of zinc borate throughout the cross sections. Thermal Gravimetric Analysis (TGA) and Differential Thermal Analysis (DTA) tests can be carried out to demonstrate superior fire retardancy to untreated wood samples.

What is claimed is:

1. Wood comprising:
    a) an aqueous composition comprising one or more solid particles of an additive dispersed in water having diameters in the range of 0.001 to 25 microns;
    b) wherein at least some of the particles penetrate the surface of the wood and are distributed throughout a cross section of the wood; and
    c) wherein the additive is one or more waxes selected from the group consisting of paraffin wax, olefin wax, petroleum wax, carnauba wax, polyethylene wax, silicone wax, polypropylene wax, PTFE wax and synthetic wax.

2. Wood of claim 1, wherein said aqueous composition further comprises an additive which is carbon black, black iron oxide, zinc oxide, titanium dioxide, or an aluminum flake pigment.

3. Wood of claim 2, wherein said aqueous composition further comprises a biocide.

4. Wood of claim 3, wherein said biocide is solid.

5. Wood of claim 4, wherein said solid biocide is copper or a copper compound.

6. Wood of claim 2, wherein said aqueous composition further comprises a colorant.

7. Wood of claim 2, wherein said aqueous composition further comprises one or more organic pigments.

8. Wood of claim 2, wherein said aqueous composition further comprises one or more inorganic pigments.

* * * * *